(12) United States Patent
Ewing et al.

(10) Patent No.: US 6,555,086 B2
(45) Date of Patent: *Apr. 29, 2003

(54) HYDROGEN FLUORIDE RECOVERY PROCESS

(75) Inventors: Paul Nicholas Ewing; Charles John Shields, both of Warrington; Robert Elliott Low, Northwich, all of (GB)

(73) Assignee: Ineos Fluor Holdings Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/402,681

(22) PCT Filed: Apr. 6, 1998

(86) PCT No.: PCT/GB98/01016

§ 371 (c)(1),
(2), (4) Date: Oct. 7, 1999

(87) PCT Pub. No.: WO98/45209

PCT Pub. Date: Oct. 15, 1998

(65) Prior Publication Data

US 2002/0156331 A1 Oct. 24, 2002

(30) Foreign Application Priority Data

Apr. 9, 1997 (GB) ............................. 9707176

(51) Int. Cl.[7] ................................. C01B 7/19
(52) U.S. Cl. .................. 423/484; 423/483; 423/488; 423/240 R; 568/682; 568/683; 570/134; 570/164; 570/165; 570/166; 570/168; 570/169; 570/170; 570/177; 570/178; 570/179; 570/180
(58) Field of Search ............... 568/682, 683; 570/134, 164, 165, 166, 168, 169, 170, 177, 178, 179, 180; 423/484, 488, 240 R, 483; 203/28, 39

(56) References Cited

U.S. PATENT DOCUMENTS

| 3,947,558 | A |   | 3/1976  | van Eijl         | 423/483 |
| 5,032,371 | A | * | 7/1991  | Buehler          | 423/484 |
| 5,276,225 | A |   | 1/1994  | Berthe           | 570/178 |
| 5,362,469 | A |   | 11/1994 | Seseke-Koyro et al. |      |
| 5,382,724 | A |   | 1/1995  | Ohno et al.      | 570/178 |
| 5,616,819 | A |   | 4/1997  | Boyce et al.     | 570/167 |
| 5,632,966 | A |   | 5/1997  | Van Der Puy et al. | 423/484 |
| 5,707,497 | A |   | 1/1998  | Galland et al.   | 203/75  |
| 5,948,381 | A |   | 9/1999  | Eibeck et al.    | 423/484 |
| 6,001,796 | A |   | 12/1999 | Pham et al.      | 510/408 |

FOREIGN PATENT DOCUMENTS

| EP | 583551       |         | 2/1994  |          |
| EP | 0 596 514 A  |         | 5/1994  |          |
| GB | 1077363      |         | 7/1967  |          |
| GB | 1078527      |         | 8/1967  |          |
| GB | 1141260      |         | 1/1969  |          |
| GB | 1 332 968 A  |         | 10/1973 |          |
| WO | 94 20412 A   |         | 9/1994  |          |
| WO | 95 27688 A   |         | 10/1995 |          |
| WO | 97 13719 A   |         | 4/1997  |          |
| WO | WO97/13719   |         | 4/1997  | ............. C01B/7/19 |

OTHER PUBLICATIONS

Jache et al, J. Phys. Chem., vol. 56, 1952, pp. 1106–1109.
Winsor et al, J. Am. Chem. Soc., vol. 70, 1958, pp. 1500–1502.
DATABASE WPI Section Ch, Week 9420–Derwent Publications Ltd., London, GB; Class E16, AN94–163857 –XP002020352 –& JP, A, 06 107 570 (SHOWA DENKO K), Apr. 19, 1994 —Abstract.
DATABASE WPI –Section Ch, Week 9333–Derwent Publications Ltd., London, GB; Class E16, AN93–261601 –XP002020353 –& JP, A, 05 178 768 (SHOWA DENKO KK), Jul. 20, 1993 –Abstract.
DATABASE WPI –Section Ch, Week 7502 –Derwent Publications Ltd., London, GB; AN 75–02816w –XP002020354 –& JP, A, 49 045 842 (ELECTRO CHEM IND CO., LTD.), Dec. 6, 1974 –Abstract.
DATABASE WPI –Week 7718 –Derwent Publications Ltd., London, GB; AN 77–31432y–XP002020355 –& JP, A, 50 097 594 (MITSUBISHI GAS CHEM IND), Aug. 2, 1975–Abstract.
McCraw–Hill Encyclopedia of Chemistry, 2nd Edition, 1993, S.P. Parker, pp. 507,508 and 1068 to 1071.
The Textbook of Physical Chemistry, 2nd Edition, 1946, S. Glasstone, pp. 976 and 977.

* cited by examiner

Primary Examiner—Rosalynd Keys
(74) Attorney, Agent, or Firm—Cook, Alex, McFarron, Manzo, Cummings & Mehler, Ltd.

(57) ABSTRACT

Processes for separating and recovering hydrogen fluoride from a gaseous mixture of an organic compound and hydrogen fluoride are disclosed. The processes include contacting the gaseous mixture with a solution of an alkali metal fluoride in hydrogen fluoride, separating a gas phase depleted in hydrogen fluoride and containing the organic compound from a liquid phase, and recovering hydrogen fluoride from the liquid phase.

17 Claims, 1 Drawing Sheet

HYDROGEN FLUORIDE RECOVERY PROCESS

This application is a 371 of PCT/GB98/01016, filed Apr. 6, 1998.

This invention relates to a hydrogen fluoride recovery process and particularly to a process for separating hydrogen fluoride from gaseous organic compounds and recovering the separated hydrogen fluoride. The invention is particularly useful for recovering hydrogen fluoride from mixtures containing minor proportions, for instance less than 25% by weight, of hydrogen fluoride and for recovering hydrogen fluoride from mixtures in which the organic compound(s) and hydrogen fluoride form an azeotropic or near-azeotropic composition. A particular embodiment of the process resides in separating hydrogen fluoride from halogen-containing organic compounds, notably fluorine-containing organic compounds, and recovering the hydrogen fluoride.

Fluorine-containing organic compounds such as hydrofluorocarbons (HFCs), hydrochloro-fluorocarbons (HCFCs) and chlorofluorocarbons (CFCs) are often produced by reacting a halocarbon starting material containing one or more atoms other than fluorine, especially chlorine atoms, with hydrogen fluoride in the liquid phase or the gaseous phase in the presence of a fluorination catalyst. The product from such reactions comprises the desired fluorine-containing organic compound, organic by-products, hydrogen chloride and unreacted hydrogen fluoride and other starting materials and it is desirable to separate these materials and recover as much as possible of the hydrogen fluoride for re-use. A proportion of the hydrogen fluoride usually can be separated and recovered by distillation but the resulting distillate usually contains residual hydrogen fluoride, especially in cases where the organic compound(s) and hydrogen fluoride form an azeotrope. This residual hydrogen fluoride is usually removed from the organic compound(s) by scrubbing the product stream with water or preferably aqueous alkali and the aqueous scrubbing liquor is then disposed of after appropriate waste water treatment. Whilst aqueous scrubbing is an effective way of removing hydrogen fluoride from the organic compound(s), it tends to be expensive in terms of hydrogen fluoride loss from the process and it is desirable to separate as much as possible and preferably essentially all of the hydrogen fluoride from the product stream before aqueous scrubbing.

According to the present invention there is provided, in a first aspect, a process for separating and recovering hydrogen fluoride from a gaseous mixture of an organic compound and hydrogen fluoride which comprises contacting the gaseous mixture with a solution of an alkali metal fluoride in hydrogen fluoride, separating a gas phase depleted in hydrogen fluoride and containing the organic compound from a liquid phase enriched in hydrogen fluoride and recovering hydrogen fluoride from the liquid phase enriched in hydrogen fluoride.

Whilst any alkali metal fluoride may be used, we prefer potasssium fluoride or caesium fluoride, especially caesium fluoride. If desired, mixtures of two or more alkali metal fluorides may be employed.

The solution of alkali metal fluoride in hydrogen fluoride may be essentially anhydrous if desired. As an alternative, a solution of an alkali metal fluoride in aqueous hydrogen fluoride may be employed.

The mixture of organic compound(s) and hydrogen fluoride being treated may be essentially anhydrous since anhydrous hydrogen fluoride is essentially non-corrosive. Where the solution of alkali metal fluoride in hydrogen fluoride is essentially anhydrous, the mixture of organic compound(s) and hydrogen fluoride is preferably essentially anhydrous. Whilst water may be present in the process, the advantage of non-corrosivity associated with anhydrous hydrogen fluoride is reduced by the presence of water. An aqueous solution however provides the advantage that, for a given concentration of alkali metal in the solution, a higher level of recovery of hydrogen fluoride from the mixture of organic compound and hydrogen fluoride may be secured. Accordingly, an anhydrous or an aqueous solution will be selected according to the particular advantage which is desired in a given process.

In order to improve the yield of hydrogen fluoride recovered from the said gaseous mixture, the gas phase depleted in hydrogen fluoride may subsequently be contacted again with a solution of an alkali metal fluoride in hydrogen fluoride from which a further gas phase further depleted in hydrogen fluoride and a further liquid phase enriched in hydrogen fluoride may be recovered. This procedure may be repeated as often as desired. The first and, if present, subsequent separation step(s) may suitably be carried out in one or more mixer/settler units or in a liquid/liquid extraction, for example a packed column as desired. If desired, a series of bubble columns may be employed for successive separation steps.

The gas phase depleted in hydrogen fluoride may be separated and treated in an appropriate manner such as by subjecting to distillation, for example in a distillation column, to recover the organic compound and/or to obtains recycle stream for feeding to an upstream point in the process, for example the reactor in which the desired organic compound is produced. This phase, whilst depleted in hydrogen fluoride, will usually contain some residual hydrogen fluoride and during distillation to recover the desired organic compound will typically provide one or more streams containing hydrogen fluoride which may be recycled. The recycle stream(s) may be fed to the reactor in which the organic compound is produced, a point upstream of the reactor so as to supplement a feed stock or to a process stream containing the organic compound, for example the mixture of an organic compound and hydrogen fluoride as described in the first aspect of the invention as desired. Any hydrogen fluoride which remains in the recovered organic compound can be recovered for example by distillation or removed by aqueous scrubbing.

The liquid phase enriched in hydrogen fluoride will usually be subjected to a separation process, preferably distillation, to recover essentially anhydrous hydrogen fluoride therefrom. The separation may be carried in any conventional separation apparatus apparatus for example a distillation column, but is preferably carried out in a flash vessel, for example a single-stage flash vessel which is suitably equipped with a reboiler and condenser.

The hydrogen fluoride recovered from the liquid phase can be collected for use in another reaction or recycled to an upstream process step, for example the reactor in which the organic compound is produced or a suitable feed stock line in the process. This liquid phase enriched in hydrogen fluoride extracted from the stream being treated will usually also contain some organic compound(s) extracted from the stream being treated. Distillation of the phase suitably removes any such organic compound(s) together with hydrogen fluoride; this mixture may then be subjected to further separation to remove at least a part of the hydrogen fluoride from the organic compound. The organic compound (s) may then be recycled as described above, for example to the reactor in which the desired organic compound is produced or to a process stream containing the organic compound.

The solution of alkali metal fluoride in hydrogen fluoride obtained as residue on separating the liquid phase enriched in hydrogen fluoride to recover hydrogen fluoride can be recycled to the process and re-used to extract hydrogen fluoride from the mixture being treated.

The amount of alkali metal fluoride in the extractant solution may vary within wide limits, depending upon the particular organic compound(s) in the mixture being treated and the solubility of the alkali metal fluoride in the hydrogen fluoride. The efficacy of the recovery of hydrogen fluoride from the process is influenced by the partial pressure of the hydrogen fluoride in the gaseous stream depleted in hydrogen fluoride which is itself influenced by the concentration of the alkali metal fluoride in the solution. The overall pressure in the separation step may influence the efficacy of recovery as variation thereof may, as a result of a phase change, alter the level of the organic compound in the gaseous phase depleted in hydrogen fluoride which will thus cause a variation in the partial pressure of hydrogen fluoride in that phase. As a guide, the concentration of alkali metal fluoride, for example caesium fluoride, will typically be from about 20% to about 80% by weight and preferably not more than about 70%. Where potassium fluoride is employed it is suitably present at a level from 20 to 40% by weight. However, it is to be understood that amounts outside the broad range may be appropriate in certain cases; saturated solutions may be advantageous in some cases.

The treatment of the gaseous mixture with the solution of alkali metal fluoride in hydrogen fluoride may be effected under any combination of temperature and pressure conditions whereby the mixture being treated is in the gaseous phase and the alkali metal fluoride solution is in the liquid phase. Atmospheric, superatmospheric or subatmospheric pressure may be employed although we prefer to employ superatmospheric pressure up to about 30 bara. The operating temperature will usually be from about −30° C. to about 50° C., preferably from about 0° C. to about 35° C. although it is to be understood that lower or higher temperatures may be employed if low or high pressure is employed.

The process of the invention can be applied to mixtures containing any amount of hydrogen fluoride although it is advantageous in the case of mixtures containing large amounts of hydrogen fluoride to remove some of the hydrogen fluoride by simple distillation before treating the mixtures according to the invention. Thus the product stream from a reactor in which the organic compound(s) is/are produced will usually be distilled and if desired otherwise treated to remove some hydrogen fluoride, any hydrogen chloride which may be present and by-products so as to provide a concentrated mixture for treatment according to the invention. Usually, the mixture to be treated will contain less than about 20% by weight, typically less than about 10% by weight of hydrogen fluoride.

The process is applicable to separation and recovery of hydrogen fluoride from mixtures thereof with any organic compound provided that the partial pressure of hydrogen fluoride in the gas stream depleted in hydrogen fluoride is lower than that of the hydrogen fluoride in the gaseous mixture which is to be treated. Of particular interest is the treatment of mixtures containing organic compounds which form an azeotropic or azeotrope-like composition with hydrogen fluoride and from which the hydrogen fluoride cannot be removed by simple distillation. Most hydrofluorocarbons, hydrochlorofluorocarbons and hydrofluoroethers form azeotropes or azeotrope-like mixtures with hydrogen fluoride and the treatment of such mixtures is a preferred embodiment of the invention, especially the treatment of mixtures wherein the organic compound is a hydrofluoroalkane, a hydrochlorofluoroalkane, a chlorofluoroalkane or a hydrofluoroether. It is to be understood, however, that the invention is not limited to the treatment of specific types of organic compound but is applicable to all organic compounds from which the separation and removal of hydrogen fluoride is not readily achieved by simple distillation. Preferably, the organic compound is a halogen-containing organic compound, especially a fluorine-containing organic compound and more preferably a hydrofluorocarbon compound.

Where the organic compound is a hydrofluoroalkane, hydrochlorofluoroalkane or chlorofluoroalkane, it will usually contain from 1 to 6 carbon atoms and preferably from 1 to 4 carbon atoms. Particular embodiments of the process reside in the treatment of mixtures wherein the organic compound is one or more of 1,1,1,2-tetrafluoroethane [HFC 134a], 1,1,2,2-tetrafluoroethane [HFC 134], chloro-1,1,1-trifluoroethane [HCFC 133a], chlorotetrafluoroethane [HCFC124/124a], pentafluoroethane [HFC 125], difluoromethane [HFC 32], chlorodifluoromethane [HCFC 22],1,1-difluoroethane [HFC 152a], 1,1,1-trifluoroethane [HFC 143a], 1,1,1,3,3 pentafluoropropane [HFC 245fa], 1,2,2,3,3-pentafluoropropane [HFC 245ca] and 1,1,1,2,3,3,3-heptafluoropropane [HFC 227ea]. Where the organic compound is a hydrofluoroether, it may contain from 2 to 8 carbon atoms and usually 2 to 6 carbon atoms. A preferred embodiment of the invention resides in treating a mixture in which the organic compound is one or more dimethyl ether, for example bis(fluoromethyl) ether [BFME], 1,1-difluorodimethyl ether, 1,1,1-trifluorodimethyl ether and pentafluorodimethyl ether.

Another aspect of the invention provides a process for the production of a fluorine-containing organic compound by reacting an organic, preferably halocarbon, starting material with hydrogen fluoride in the gaseous phase or in the liquid phase optionally in the presence of a fluorination catalyst, to produce a product stream comprising the fluorine-containing organic compound and unreacted hydrogen fluoride, contacting the product stream, preferably a gaseous product stream, with a solution of an alkali metal fluoride in hydrogen fluoride, separating a gas phase depleted in hydrogen fluoride and containing the organic compound from a liquid phase enriched in hydrogen fluoride and recovering hydrogen fluoride from the liquid phase enriched in hydrogen fluoride.

The product stream may be treated prior to contact with the solution of alkali metal fluoride in hydrogen fluoride for example in order to remove compounds other than the desired fluorine-containing compound from the product stream. The treatment, where employed, may include any conventional separation process for example distillation and phase separation.

The organic starting material is selected according to the desired fluorine-containing organic compound. The starting material may be a halocarbon and so contain one or more halogen atoms, especially chlorine and/or fluorine atoms, and may also contain hydrogen. For example, to produce difluoromethane, bis(fluoromethyl)ether (BFME) or methylene chloride may be employed as the halocarbon starting material, to produce 1,1,1,2-tetrafluoroethane the starting material may comprise trichloroethylene and/or 1,1,1-trifluorochloroethane, to produce pentafluoroethane, perchloroethylene may be employed as the halocarbon starting material and to produce chlorodifluoromethane, chloroform may be suitably employed as the halocarbon starting material.

However, for certain products, the starting material need not contain a halogen atom, for example. BFME may be produced by contacting hydrogen fluoride with formaldehyde as described in our earlier prior published European Patent Applications EP-A-518506 or EP-A-612309, the disclosures of which are incorporated herein by reference. Another example of a halogen-free organic starting which may be employed is acetylene which may be reacted with hydrogen fluoride to produce HFC 152a.

Difluoromethane may be produced from BFME in the liquid or gaseous phase, for example as described in our earlier prior puiblished European Patent Application EP-A-518506. In a gaseous phase reaction the BFME starting material may be introduced into a heating zone in undiluted form although, depending upon the process employed for the production of the BFME vapour, the material may be fed into the heating zone in conjunction with a diluent such as an inert carrier gas, for example nitrogen. The temperature to which the BFME is heated to produce difluoromethane is such that the bis(fluoromethyl)ether is in the vapour phase and the temperature will typically be at least 80° C., preferably at least 200° C. and more preferably at least 250° C. The temperature need be no higher than about 500° C., although higher temperatures, say up to about 700° C., may be used if desired.

The BFME is suitably heated in the presence of hydrogen fluoride vapour. The hydrogen fluoride may be used as the diluent or carrier gas with which the BFME is introduced into the reaction zone or the hydrogen fluoride may be introduced into the reaction zone separately.

In producing 1,1,1,2-tetrafluoroethane by fluorinating trichloroethylene to produce 1,1,1-trifluoro-2-chloroethane (HFC-133a) which is then converted to HFC-134a by fluorination. HF is suitably employed as the fluorinating agent. Preferably the reaction is carried out in the presence of a catalyst for at least one and desirably both reaction stages and is suitably conducted in the gaseous phase. The quantity of HF employed may be from 10 to 100, preferably 15 to 60, moles of HF per mole of trichloroethylene. Where the reaction involves fluorination of 1,1,1-trifluoro-2-chloroethane, the amount of HF may be up to 10 moles, and preferably from 2 to 6 moles, of HF per mole of 1,1,1-trifluoro-2-chloroethane.

The process for the manufacture of 1,1,1,2-tetrafluoroethane may be carried out in accordance with the reaction sequence described and claimed in our prior published European Patent Application No. 449617, the disclosure of which is incorporated herein by reference.

Pentafluoroethane may be produced by any of the processes described in our prior published International Patent Applications WO95/27688 and WO95/16654, the disclosures of which are incorporated herein by reference.

Chlorodifluoromethane [HCFC 22] may be produced by fluorination of chloroform with hydrogen fluoride. The fluorination may take place in the liquid phase in the presence of a fluorination catalyst for example a transition metalk fluoride, for example, a fluoride of tantalum or of niobium. As an example fluorination in the liquid phase may be carried out using $SbCl_{(5-x)}F_x$, x=0–5 at temperatures typically between 50° C.–180° C. As desired, intermittent addition of chlorine may be used to maintain the catalyst in the pentavalent state. The reaction pressure can vary widely between subatmospheric pressure to 50 Barg. More preferably the reaction pressure lies within the range 5 Barg–30 Barg. Chloroform and hydrogen fluoride are suitably introduced to a reactor (in either liquid or vapour phase), usually in a molar ratio of about 1:2 to produce a product stream which typically contains chlorodifluoromethane, hydrogen chloride, fluorodichloromethane [HCFC 21] and unreacted hydrogen fluoride. This stream may then be treated, for example by distillation, to remove certain components, for example, hydrogen chloride and fluorochloromethane, and so provide a stream of chlorodifluoromethane and hydrogen fluoride from which hydrogen fluoride may then be recovered by the process according to the first aspect of the invention. The fluorination reaction using hydrogen fluoride may be carried out in the presence of a catalyst; any conventional catalyst described in the prior art may be employed and will be selected according to the starting materials and the desired fluorine-containing product.

The catalyst may be for example, a metal, for example an s-block metal such as calcium, a p-block metal such as aluminium, tin or antimony, an f-block metal such as lanthanum or a d-block metal such as nickel, copper, iron, manganese, cobalt and chromium or alloys thereof; a metal oxide, for example chromia or alumina, a metal fluoride, for example, aluminium, manganese or chromium fluoride, or a metal oxyfluoride, for example an oxyfluoride of one of the aforementioned metals. The metal in the catalyst is preferably a d- or -p-block metal, and more preferably chromium, aluminium, or a Group V111a metal. The catalyst may be promoted with other metals for example zinc and nickel. If used, the alloy may also comprise other metals, for example molybdenum. Examples of preferred alloys include Hastelloy and stainless steel is especially preferred.

The fluorination catalyst may be conditioned for example by passing substantially dry HF with or without nitrogen diluent over the catalyst at about 250 to 450° C. whilst regeneration of the catalyst may be carried out using a mixture of substantially dry HF and an oxidising gas such as air or oxygen, at a temperature in the range of 300 to 500° C. as disclosed in our prior EP-A-475693, the disclosure of which is incorporated herein by reference.

BRIEF DESCRIPTION OF DRAWING

The sole FIGURE of the drawing is a schematic representation of a plant for carrying out the preferred process of the present invention for recovery of HF.

The process is illustrated in respect of the treatment of a product stream comprising chlorodifluoromethane [HCFC 22] produced by a fluorination process and containing unreacted hydrogen fluoride.

Figure 1:
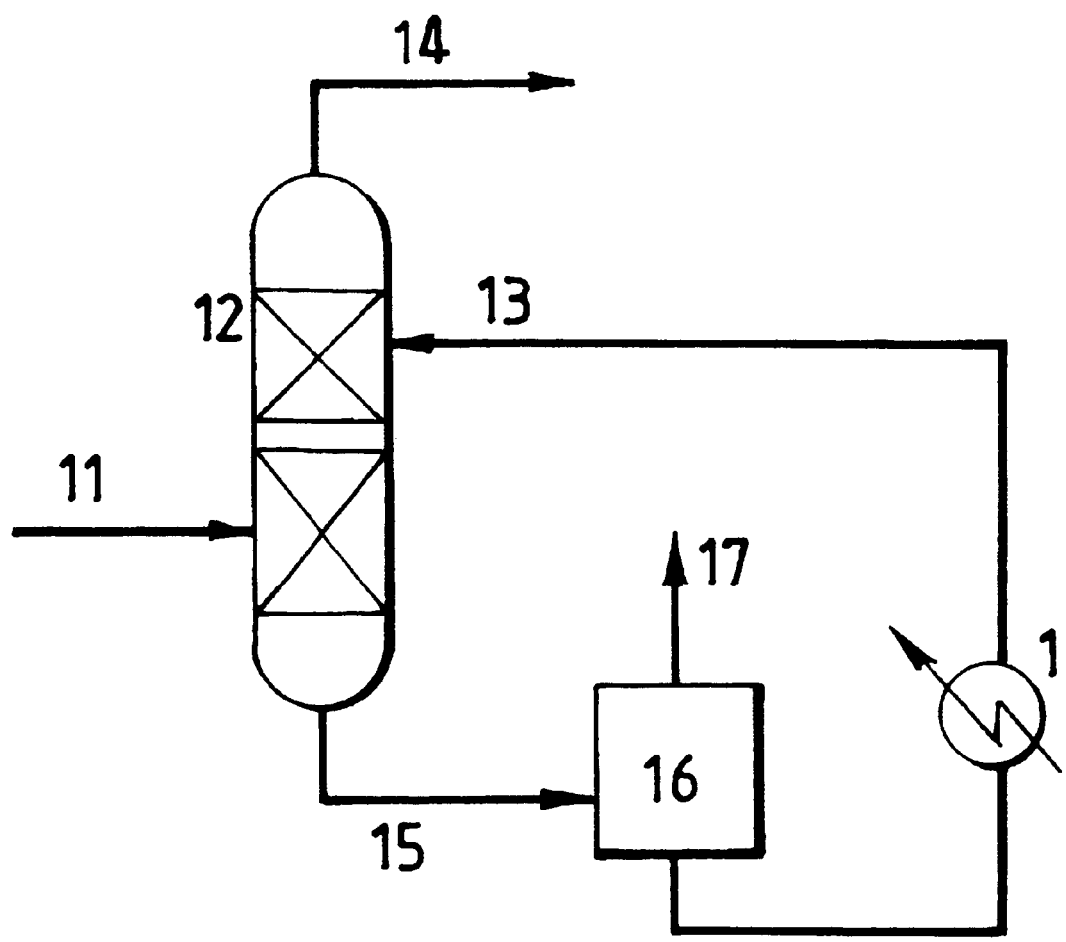

The product stream from a fluorination reactor used to produce HCFC 22 is subjected to primary purification (not shown), for example by distillation and the resulting gaseous phase process stream 11 of HCFC 22 and hydrogen fluoride containing a mixture of HCFC 22 and hydrogen fluoride in the vapour phase is introduced to a column 12, in which it is contacted with stream 13, containing a solution of alkali metal fluoride in hydrogen fluoride whereby hydrogen fluoride is separated from the HCFC 22. Stream 14, containing HCFC 22 vapour and less hydrogen fluoride than stream 11 is removed from the top of the column and subjected to further processing (not shown) to recover essentially pure HCFC 22. Stream 15, a solution of alkali metal fluoride in hydrogen fluoride containing more hydrogen fluoride than stream 13, is removed from the bottom of column 12. Stream 15 is fed to a separation stage 16, for example a single stage flash vessel, in which hydrogen fluoride is separated and withdrawn as stream 17 for collection or recycle, while a bottoms stream 13, comprising the extractant solution of alkali metal fluoride in hydrogen fluoride, is withdrawn from vessel 16, cooled in heat exchanger 18, and recycled to column 12.

In a preferred embodiment of the process, the separation stage 16 may be replaced by a single-stage flash vessel comprising a reboiler equipped with a condenser or alternatively a distillation column.

The process of the invention may be operated as a batch process but preferably is operated as a continuous process.

The invention is illustrated but in no way limited by the following example.

EXAMPLE 1

A 500 ml PTFE flask was charged with 192 g of anhydrous HF, 294 g of CsF and 1 g of HCFC 22. This resulted in a vapour and liquid phase being formed inside the flask. The mixture was allowed to equilibrate at atmospheric pressure and 23° C. Following equilibration a sample was removed from the head space and its composition determined as HF: 1.34% w/w HCFC 22: 98.66% w/w This compares with the composition of the HCFC22/HF binary azeotrope at atmospheric pressure of HF: 3.75% w/w HCFC 22: 96.25% w/w From the above, it is clear that a solution of CsF in anhydrous HF can reduce the HF content of a gaseous mixture of HCFC 22 and HF to below that of the azeotropic composition and thus provide for effective separation and recovery of hydrogen fluoride.

EXAMPLE 2

A 500 ml metal vessel was evacuated and charged with 200 mls of a solution of 63.5% w/w CsF dissolved in anhydrous HF and pressurized to 6 bara by addition of HCFC 22 vapour. The contents of the vessel were well mixed and allowed to equilibrate at room temperature. A sample of the vapour phase was removed for analysis and found to contain:

HCFC 22 99.8wt %

HF 0.2% wt

This composition is enriched in HCFC 22, compared with the HCFC 22/HF azeotropic composition of approximately 96wt % HCFC 22 and 4wt % HF.

Comparative Example A

The procedure of Example 2 was repeated, using liquid anhydrous HF with no CsF present. A sample of the vapour phase was removed for analysis and found to contain:

HCFC 22 90.6wt %

HF 9.4% wt

It is evident that the concentration of HF in the vapour phase in this case is significantly higher than when there is no CsF present thus illustrating the preferential partitioning effect of the alkali metal fluoride solution.

EXAMPLES 3 to 7

The procedure of Example 2 was repeated with different hydrofluorocarbons and hydrocarbons. A sample of the vapour phase was removed and analysed. The results are tabulated below.

| Example | Component | Average Pressure (barA) | % w/w HF in vapour | % w/w Organic in Vapour |
|---|---|---|---|---|
| 3 | HFC 125 | 10.5 | 0.08 | 99.92 |
| 4 | HFC 32 | 12 | 0.20 | 99.8 |
| 5 | HFC 134a | 4.8 | 0.23 | 99.77 |
| 6 | HFC 227 | 4.4 | 0.34 | 99.66 |
| 7 | Propane | 8.6 | 0.38 | 99.62 |

It is evident that the equilibrium concentration of HF in the vapour phase is very low in all cases.

EXAMPLE 8

In this Example, the composition of the vapour phase over a solution of CsF in anhydrous HF was determined by charging a solution of 55wt % CsF in HF to an enclosed vessel equipped with an inlet and outlet port through which nitrogen could be sparged to an aqueous scrubbing train. The solution was heated and nitrogen was sparged slowly through the vessel until the solution reached a composition of 55%, 60wt % and then 65% CsF in HF with a vapour pressure of I bara. The temperatures required to generate a vapour pressure of 1 bara over HF solutions of varying CsF concentration are tabulated below:

| Wt % CsF in solution | Temp to generate 1 bara vapour pressure C |
|---|---|
| 55 | 72 |
| 60 | 87 |
| 65 | 100 |

The scrubbing train was analyzed for both HF and CsF. The results at each temperature indicated that the vapour phase material sparged out of the vessel comprised 100.00wt % HF and there was no CsF detected.

What is claimed is:

1. A process for separating and recovering hydrogen fluoride from a gaseous mixture of an organic compound and hydrogen fluoride which comprises contacting the gaseous mixture with a solution of an alkali metal fluoride in hydrogen fluoride, separating a gas phase depleted in hydrogen fluoride and containing the organic compound from a liquid phase enriched in hydrogen fluoride and recovering hydrogen fluoride from the liquid phase enriched in hydrogen fluoride.

2. A process for separating and recovering hydrogen fluoride from a gaseous mixture of an organic compound and hydrogen fluoride which comprises contacting the gaseous mixture with an essentially anhydrous solution of an alkali metal fluoride in hydrogen fluoride, separating a gas phase depleted in hydrogen fluoride and containing the organic compound from a liquid phase enriched in hydrogen fluoride and recovering hydrogen fluoride from the liquid phase enriched in hydrogen fluoride.

3. A process for separating and recovering hydrogen fluoride from a gaseous mixture of an organic compound and hydrogen fluoride which comprises contacting the gaseous mixture with a solution of an alkali metal fluoride in aqueous hydrogen fluoride, separating a gas phase depleted in hydrogen fluoride and containing the organic compound from a liquid phase enriched in hydrogen fluoride and recovering hydrogen fluoride from the liquid phase enriched in hydrogen fluoride.

4. A process as claimed in any preceding claim wherein the alkali metal fluoride comprises potassium fluoride and/or caesium fluoride.

5. A process as claimed in claim 1, 2 or 3 wherein hydrogen fluoride is recovered from the liquid phase enriched in hydrogen fluoride by distillation.

6. A process as claimed in claim 5 in which the distillation is carried out in a flash vessel or a distillation column.

7. A process as claimed in claim 1, 2 or 3 in which at least part of any residual hydrogen fluoride-containing alkali metal fluoride which remains after recovering hydrogen fluoride from the liquid phase enriched in hydrogen fluoride is recycled for contact with the mixture to be separated.

8. A process as claimed in claim 1, 2 or 3 in which hydrogen fluoride is recovered from a mixture containing less than 25% by weight of hydrogen fluoride.

9. A process as claimed in claim 8 in which said mixture to be treated contains less than 10% by weight of hydrogen fluoride.

10. A process as claimed in claim 1, 2 or 3 in which the organic compound(s) and hydrogen fluoride form an azeotropic or near-azeotropic composition.

11. A process as claimed in claim 1, 2 or 3 in which a stream comprising hydrogen fluoride is derived from the gaseous phase depleted in hydrogen fluoride and is recycled to the reactor in which the desired organic compound is produced and/or to a stream comprising the organic compound.

12. A process as claimed in claim 1, 2 or 3 in which the concentration of alkali metal fluoride in the solution of alkali metal fluoride in hydrogen fluoride is from about 20% to about 80% by weight.

13. A process as claimed in claim 1, 2 or 3 in which the organic compound comprises a halogen-containing organic compound.

14. A process for the production of a fluorine-containing organic compound by reacting an organic starting material with hydrogen fluoride in the gaseous phase or in the liquid phase optionally in the presence of a fluorination catalyst to produce a gaseous product stream comprising the fluorine-containing organic compound and unreacted hydrogen fluoride, contacting the product stream with a solution of an alkali metal fluoride in hydrogen fluoride, separating a gas phase depleted in hydrogen fluoride and containing the organic compound from a liquid phase enriched in hydrogen fluoride and recovering hydrogen fluoride from the liquid phase enriched in hydrogen fluoride.

15. A process as claimed in claim 14 in which the organic compound comprises a hydrofluoroalkane, a hydrochlorofluoroalkane, a chlorofluoroalkane and/or a hydrofluoro ether.

16. A process as claimed in claim 15 in which the organic compound is selected from one or more of an 1,1,1,2-tetrafluoroethane [HFC 134a], 1,1,2,2-tetrafluoroethane [HFC 134], chloro-1,1,1-trifluoroethane [CFC 133a], chlorotetrafluoroethane [HCFC124/124a], pentafluoroethane [HFC 125], difluoromethane [HFC 32], chlorodifluoromethane [HCFC 22] 1,1-difluoroethane [HFC 152a], 1,1,1-trifluoroethane [HFC 143a], 1,1,1,3,3 pentafluoropropane [HFC 245fa], 1,2,2,3,3-pentafluoropropane [HFC 245ca] 1,1,1,2,3,3,3-heptafluoropropane [HFC 227ea], bis(fluoromethyl) ether [BFME], 1,1-difluorodimethyl ether, 1,1,1-trifluorodimethyl ether and pentafluorodimethyl ether.

17. A process as claimed in claim 14 in which the product stream is treated prior to contact with tile solution of the alkali metal fluoride in hydrogen fluoride.

* * * * *